United States Patent [19]

Di Schiena

[11] Patent Number: 4,698,361

[45] Date of Patent: Oct. 6, 1987

[54] TRIS-(HYDROXYMETHYL) AMINOMETHANE SALT OF 4-CHLORO-N-FURFURYL-5-SULFAMOYL ANTHRANILIC ACID AND DIURETIC COMPOSITIONS CONTAINING THE SAME

[76] Inventor: Michele G. Di Schiena, Via Carducci, 21, 20090 Trezzano Sul Naviglio, Italy

[21] Appl. No.: 867,446

[22] Filed: May 28, 1986

[51] Int. Cl.$^4$ .................... C07D 307/52; A61K 31/34
[52] U.S. Cl. ...................................... 514/471; 549/494
[58] Field of Search ......................... 549/494; 514/471

[56] References Cited

U.S. PATENT DOCUMENTS 4,564,625  1/1986  Muschaweck et al. ............. 549/494

OTHER PUBLICATIONS

Gallardo CA 86:34265f, 86:111169g
Anon CA:84:111535g.

*Primary Examiner*—Jane T. Fan
*Attorney, Agent, or Firm*—Oblon, Fisher, Spivak, McClelland & Maier

[57] ABSTRACT

A novel chemical compound, i.e. the tris-(hydroxymethyl)aminomethane salt of 4-chloro-N-furfuryl-5-sulfamoylanthranilic acid, is described.

The novel compound is water soluble and exhibits such peculiar properties as to be fit for preparing pharmaceutical forms for parenteral or oral administration. It is useful both for human and veterinary use.

6 Claims, No Drawings

TRIS-(HYDROXYMETHYL) AMINOMETHANE SALT OF 4-CHLORO-N-FURFURYL-5-SULFAMOYL ANTHRANILIC ACID AND DIURETIC COMPOSITIONS CONTAINING THE SAME

DESCRIPTION

The present invention relates to a novel chemical compound, i.e. the tris(hydroxymethyl)aminomethane salt of 4-chloro-N-furfuryl-5-sulfamoylanthranilic acid hereinafter also referred to as Furotris, according to formula (I)

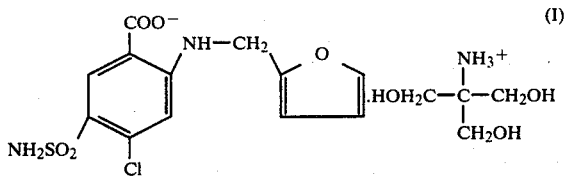

4-Chloro-N-furfuryl-5-sulfamoylanthranilic acid (usually known as Furosemide) is from a long time therapeutically employed as valuable diuretic, antihypertensive drug (The Merck Index-tenth edition).

Tris(hydroxymethyl)aminomethane (known as Tromethamol) too is from a long time therapeutically employed as corrective agent for metabolic acidosis (Repertorio Terapeutico, 6a ed.); it has, moreover, excellent buffering properties.

Furosemide is practically water insoluble and for parenteral administration its sodium salt is normally used.

The Furosemide sodium salt has the drawback of its aqueous solution giving alkaline reaction (pH: 8.9–9.3; U.S.P. XIX). The aqueous solution is, therefore, insufficiently physiologically compatible and can bring about local intolerance phenomena (f.i., high proneness to pain).

The sodium ion, moreover, exhibits serious drawbacks due to its known tendency to increase water retention and make therefore worse the relevant symptoms (edema); such a risk increases in long-term therapies, such as those required by the pathological conditions treated with Furosemide.

Furasemide sodium salt, owing to its low water solubility, is not suitable for oral preparations such as drops, wherein is known as highly important the possibility of achieving a high drug concentration.

It should be appreciated that oral preparations in drops are particularly useful in therapies with diuretic compounds in that they allow tailor-made dosage for a single patient, taking into account the illness to be cured and its development, sex and age of the patient.

The novel compound according to formula (I), which is the object of the present invention, exhibits, inter alia, peculiar properties making it particularly suitable for preparing pharmaceutical forms for injection use (intramuscular and intravenous) and for oral administration.

The novel compound according to formula (I) is highly soluble in water, its aqueous solution having a strictly physiologically compatible reaction (pH: 6-6,5) and, in view of the well-known buffering activity of Tromethamol, the novel compound consequently results as less affected by pH changes due to biological liquids (blood, gastroenteric juices, etc.).

The therapeutic activity of the novel compound according to formula (I) and of Furosemide are substantially alike; the toxicity, too, comes within the limits already known for Furosemide.

The injectable preparations of the novel compound according to formula (I) are remarkably better tolerated and this has certainly to be ascribed to their better physiological compatibility.

Even the absorption, the action time and its lenght are significantly improved, if compared with the Furosemide sodium salt.

In preparations for oral administration the novel compound according to formula (I) can be usefully employed in all pharmaceutical forms known in the art, f.i.: tablets (including the gastro-protected and release forms), capsules, granules (including the effervescent ones), syrups, drops and release microgranules.

Particularly the oral preparations in drops advantageously employ the novel compound according to formula (I), in view of the highly concentrated solutions of the active ingredient which can be obtained; such an oral form is particularly advantageous in that it allows a usefully flexible dosage, therefore more in keeping with the single pathologic cases.

Preparation methods

The novel compound according to formula (I) can be prepared by methods known in the art and essentially consisting in reacting equimolar amounts of Furosemide and Tromethamol. As reaction medium water can be employed or an appropriate organic solvent, such as methanol, isopropanol, acetone, ethanol, etc., in anhydrous form or containing variable water amounts, f.i 5–90%.

The novel compound according to formula (I) can be utilized directly in the reaction solution or it can be isilated first with methods known in the art, such as concentration, freeze-drying, precipitation with insolubilizing solvents.

EXAMPLE 1

33 g (0.1 mole) Furosemide and 12.1 g (0.1 mole) Tromethamol are added to 250 ml methanol; after shortly stirring at 30° C. a thorough solution is obtained.

The solution is filtered, the filter washed with a small amount of methanol and the clear solution evaporated under vacuum 50° C., as measured from the outside. To the resulting residue 1000 ml of acetonitrile at 30° C. are added, whereby a thorough solution is obtained.

The solution is filtered under vacuum and the filter washed with a small amount of acetonitrile; the resulting clear solution is maintained for six hours at 0° C. under stirring so as to allow complete crystallization of the novel compound according to formula (I).

The crystalline compound is isolated by filtration under vacuum, washed three times, directly on the filter, with 100 ml portions of acetonitrile and dryed in oven at 40° C.—Yield: 41,5 g (92% of theory). TLC analysis and chemical titration prove the high purity of the compound and IR analysis demonstrate the structure according to formula (I).

EXAMPLE 2

33 g (0.1 mole) Furosemide are suspended in 90 ml water and 12.1 g (0.1 mole) Tromethamol are added portionwise at room temperature by stirring; a thorough solution results with pH about 6.3.

This solution, filtered if that is the case thorough a sterilizing and pyrogens removing filter, can be directly employed for preparing injectable pharmaceutical forms and liquid pharmaceutical forms for oral administration by appropriately diluting, if necessary, with water and adding other suitable active ingredients, compatible with the novel compound.

Alternatively the novel compound can be isolated by evaporating water under vacuum.

EXAMPLE 3

Furotris—33.3 g,
Sorbitol—1.0 g.

Flavoured water balance to 100 g are introduced in a suitable dropper bottle for oral use; 20 drops=1 g solution correspond to 0,333 g Furotris or 0.243 g Furosemide.

EXAMPLE 4

33,3 g Furotris are dissolved in 700 ml distilled water; the resulting solution is filtered through a sterilizing and pyrogens removing filter.

The resulting solution is diluted up to a volume of exactly 1000 ml with sterile and pyrogen-free distilled water.

The preparation appropriately disposed into vials is suitably used for injections (intramuscular, intravenous).

I claim:

1. A compound having the formula (I):

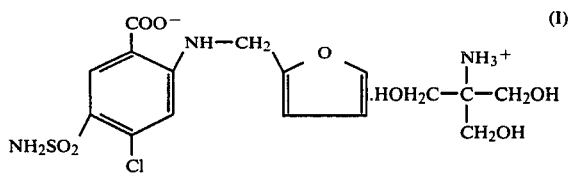

which is the tris(hydroxymethyl)aminomethane salt of 4-chloro-N-furfuryl-5-sulfamoylanthranilic acid.

2. A diuretic pharmaceutical composition comprising an effective amount of the compound of claim 1, and a pharmaceutically-acceptable excipient.

3. The composition of claim 2, which is in a form suitable for oral administration.

4. The composition of claim 2, which is in a form suitable for administration by injection.

5. The composition of claim 3, which is suitable for administration by drops.

6. The composition of claim 4, which is suitable for intramuscular or intravenous injection.

* * * * *

UNITED STATES PATENT AND TRADEMARK OFFICE
CERTIFICATE OF CORRECTION

PATENT NO. : 4,698,361
DATED : October 6, 1987
INVENTOR(S) : Michele G. Di Schiena It is certified that error appears in the above-identified patent and that said Letters Patent is hereby corrected as shown below:

On the Title Page, Item [54]

The second word in the the title is spelled incorrectly. Should read as follows:

- (HYDROXYMETHYL) -

Signed and Sealed this

Ninth Day of February, 1988

Attest:

DONALD J. QUIGG

Attesting Officer

Commissioner of Patents and Trademarks